United States Patent
Rick et al.

(10) Patent No.: US 6,304,632 B1
(45) Date of Patent: Oct. 16, 2001

(54) METHOD AND APPARATUS FOR RADIOGRAPHY HAVING AN ANTISCATTER GRID

(75) Inventors: Andreas Rick, Plaisir; Serge Muller, Guyancourt; Jean-Luc Baudry, Plaisir, all of (FR)

(73) Assignee: GE Medical Systems, S.A. (FR)

(*) Notice: Subject to any disclaimer, the term of this patent is extended or adjusted under 35 U.S.C. 154(b) by 0 days.

(21) Appl. No.: 09/415,816

(22) Filed: Oct. 12, 1999

(30) Foreign Application Priority Data

Oct. 15, 1998 (FR) .................................................. 98 12953

(51) Int. Cl.$^7$ ........................................................ G21K 1/00
(52) U.S. Cl. ................................................................ 378/155
(58) Field of Search ...................................... 378/154, 155

(56) References Cited

U.S. PATENT DOCUMENTS

| 4,803,716 | 2/1989 | Ammann et al. | 378/155 |
| 5,357,554 | 10/1994 | Schneiderman et al. | 378/155 |

*Primary Examiner*—Craig E. Church
(74) *Attorney, Agent, or Firm*—Jay L. Chaskin

(57) ABSTRACT

The movement of an anti-scatter grid in a radiography apparatus is a continuous curve having point symmetry with respect to the point whose time coordinate is equal to half the exposure time, and for which the space derivative of the time variable has two linear portions which are symmetrical with respect to a symmetry axis passing through the middle of the range of movement of the grid. The grid is moved with a high rate of movement close to the starting position and the end position.

8 Claims, 2 Drawing Sheets

METHOD AND APPARATUS FOR RADIOGRAPHY HAVING AN ANTISCATTER GRID

BACKGROUND OF THE INVENTION

The invention relates to improvement of the quality of a radiographic image of an object obtained by a radiographic X-ray unit containing an anti-diffusion or anti-scatter grid.

The invention applies advantageously but not exclusively to mammography examinations for the detection of micro-calcifications inside a breast.

A radiographic X-ray unit, used in particular in mammography, is equipped with an anti-diffusion grid arranged between the object to be radiographed, in this case a breast, and a receiver of radiographic images, for example a CCD (charge-coupled) receiver. In conventional fashion, the anti-diffusion grid is composed of a series of plates that are all directed toward the focal point of X-ray radiation emitted in the direction of the object and of the image receiver. Thus, the anti-diffusion grid allows the undiffused direct beams to pass, while the diffused beams are absorbed by the plates.

This being so, the resolution of the image receiver is generally finer than the space between two plates, which typically is of the order of 0.3 mm. The result of this is that the plates are visualized on the radiographic image obtained, which is particularly troubling in mammography because it makes detection of micro-calcifications more difficult.

One solution of this problem consists of displacing the grid during exposure, in rectilinear translation in its plane, i.e., substantially perpendicular to the plates of the anti-diffusion grid. Such translation may be effected only in one direction or, in alternating fashion, in both directions.

The quality of the image is thus improved but nevertheless remains inadequate. In addition, generation of an alternating movement is a mechanically more complicated solution.

BRIEF DESCRIPTION OF THE INVENTION

An embodiment of the invention eliminates, insofar as possible, the visible traces of the plates of the anti-diffusion grid on the radiographic film.

An embodiment of the invention obtains an improvement in the quality of the images by a mechanically simple solution for displacement of the anti-diffusion grid.

An embodiment of the invention makes it possible to obtain improved quality images by a particular displacement profile of a anti-diffusion grid.

More precisely, the invention is a method of improvement of the quality of a radiographic image of an object obtained by an X-ray unit containing an anti-diffusion grid, arranged between the object and a receiver of radiographic images, which grid is displaced in rectilinear translation in its plane, at the time that the image is taken, between a starting position and an ending position and according to a predetermined temporal law of displacement.

DETAILED DESCRIPTION OF THE INVENTION

According to a general characteristic of the invention, the law of displacement is a continuous curve exhibiting point symmetry with respect to the point whose temporal coordinate is equal to one-half of the duration of photography, and whose spatial derivative of the temporal variable exhibits two (preferably linear) portions symmetrical with respect to an axis of symmetry passing through the center of the area of displacement of the grid. In addition, the grid is displaced according to the law of displacement at a high rate of displacement in the vicinity of the starting position and of the ending position.

According to one mode of implementation of the invention, the high rate of displacement is between about three times and about ten times the value of the ratio between the area of displacement and the duration of photography. In other words, this high rate of displacement is between about three times and about ten times the value of a linear rate of displacement of the grid between the starting position and the photography position. In a preferred mode of implementation of the invention, the continuous curve is formed of two portions symmetrical with respect to the point whose temporal coordinate is equal to one-half of the said duration of photography, each of these portions representing a profile of evolution of the variable "position," a function of the square root of the variable "time."

Figure 1:
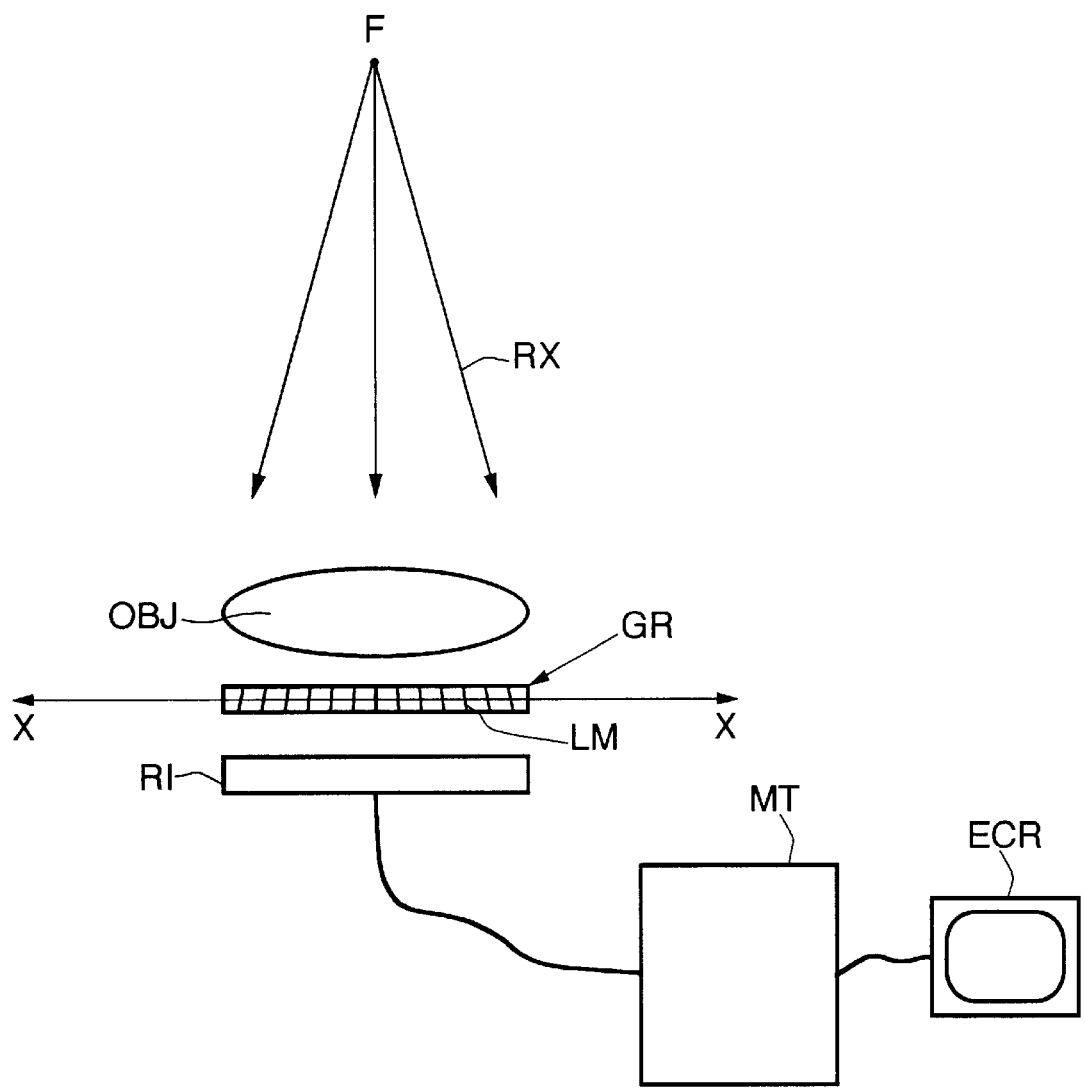
FIG. 1 is a schematic view of an X-ray device permitting implementation of the method according to an embodiment of the invention.

In FIG. 1, the reference F designates the focal point of an X-ray tube emitting a beam RX of X-rays in the direction of an object to be radiographed OBJ. The radiographic images are received on a receiver RI, comprising for example a CCD sensor. The receiver RI is connected to processing means MT structured about a microprocessor and the radiographic images may be visualized on a display screen ECR. Between the object OBJ to be radiographed and the receiver RI, there is arranged an anti-diffusion grid GR movable in translation substantially perpendicular to the radiation emitted, i.e., in the direction XX of FIG. 1. This grid is composed of a plurality of plates LM, all directed toward the focal point F. These plates, typically spaced on the order of 0.3 mm, make it possible to absorb the radiation diffused by the object and to allow only the direct radiation to pass.

In order to avoid visualization of the plates LM on the images obtained the grid GR is displaced in rectilinear translation in its plane, i.e., in the direction XX, according to a profile, predetermined at the time that each image is taken, between a starting position and an ending position.

If the "period" of the grid is designated as the distance separating the edge of one plate from the edge of the immediately adjacent plate, i.e., a distance equal to the thickness of the plate plus the distance between two adjacent plates, it has been observed that one of the principal reasons producing visualization of the plates on the images obtained is the fact that the number of grid periods that pass between the X-radiation and each pixel of the image receiver is not a whole number. In other words, the part of a grid period that does not pass between the radiation RX and a pixel of the image receiver renders the corresponding plate of the grid visible on the image obtained.

In addition, it has been observed that the act of displacing the grid at a high rate of displacement in the vicinity of the starting position and of the ending position makes it possible to reduce the visualization of traces of the grid on the radiographed image, because this contributes to a reduction of the time of exposure of incomplete periods of the grid situated at the ends of the latter.

However, it is not necessary to provide a high rate of displacement in the center of the area of displacement because, in this zone, complete grid periods pass between the X-radiation and a considered pixel of the image receiver.

In other words, because of the periodicity of the grid, the intensity of X-radiation reaching the image receiver is the temporal integral over the period of exposure of the incident energy multiplied by a coefficient of attenuation. It is this temporal integral that makes it possible to render the incomplete periods of the grid visible on the image, and to eliminate the traces of plates corresponding to complete periods of the grid that have been displaced between the radiation RX and the pixels of the sensor RI.

In a general way, the displacement profile of the grid between the starting position X0 and the ending position XM during the exposure time TP of each image (TP=T1−T0) is a continuous curve exhibiting point symmetry with respect to the point whose temporal coordinate is equal to TP/2, and whose spatial derivative dt/dx of the temporal variable has two portions symmetrical with respect to an axis of symmetry passing through the center of the area of displacement of the grid. The rate of displacement V0 in the vicinity of the starting position and of the ending position must be high, for example between about three times and about ten times the value of the ratio (XM−X0/TP) between the area of displacement and the duration of photography, i.e., three to ten times higher than the value of a linear rate of displacement.

Figure 2:
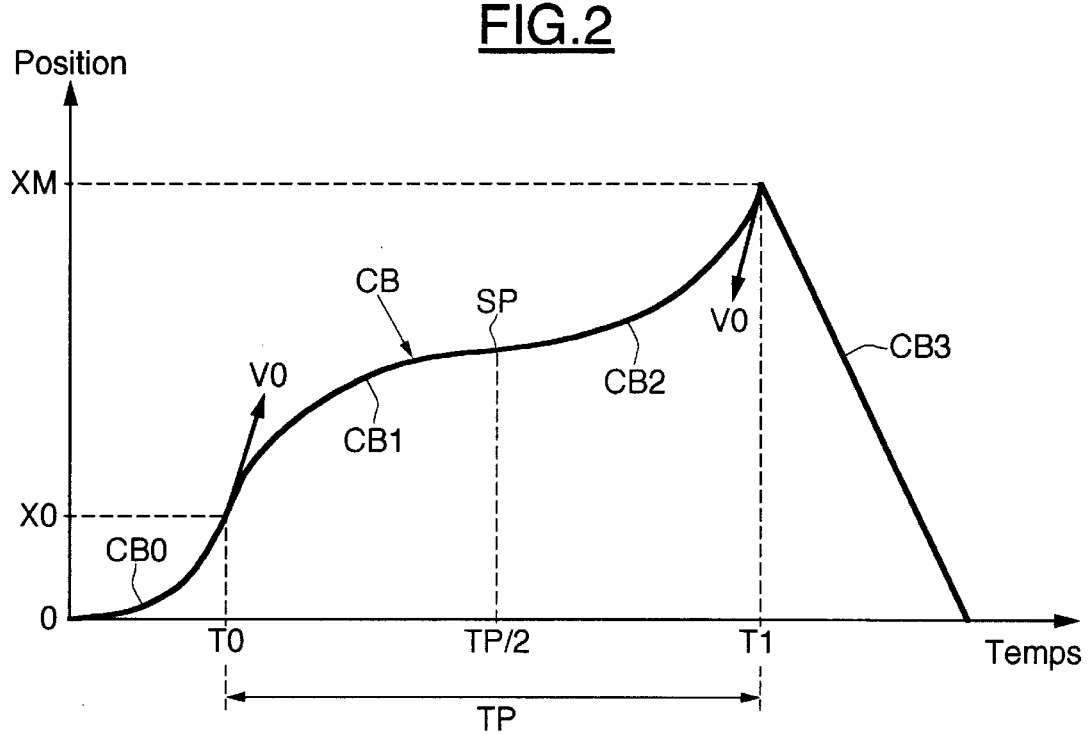
FIG. 2 illustrates a law of displacement of the grid, according to an embodiment of the invention.
Figure 3:
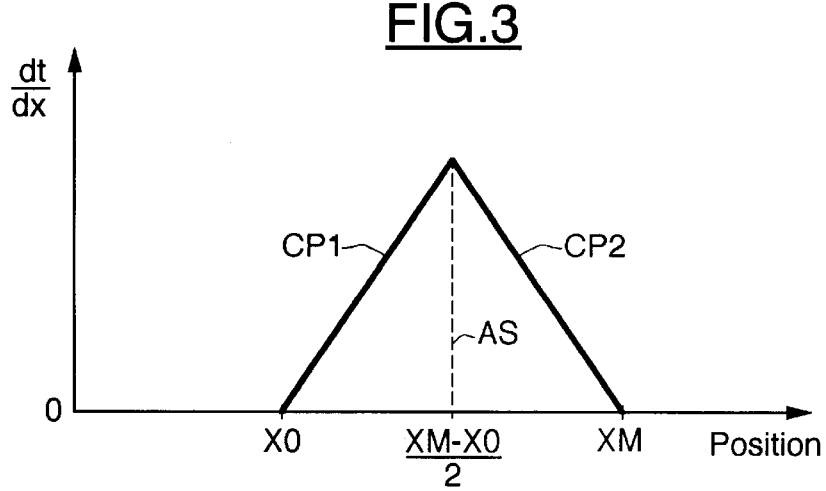
FIG. 3 illustrates the spatial derivative of the time variable of the law of displacement of FIG. 2.

The example described in FIGS. 2 and 3 shows that this continuous curve CB is formed of two portions symmetrical with respect to the point SP of temporal coordinate TP/2. Each of these portions CB1 and CB2 represents a profile of evolution of the variable "position" (X), which is a function of the square root of the variable "time" (t).

More precisely, the equation of the portion CB1 is given by the formula (1) below:

$$X(t) = Ao + b\sqrt{ct - TC0} \text{ for } t \leq TP/2 \quad (1)$$

while the equation of the portion CB2 is given by the formula (2) below:

$$X(t) = Al - b\sqrt{-ct + TC1} \text{ for } t = TP/2 \quad (2)$$

In these formulas, Ao, Al, b, c, TC0, and TC1 are constants making it possible to adjust the position of the grid to the value X0 for the instant T0 and to the value XM for the instant T1, and making it possible to join the two portions CB1 and CB2 at the point SP.

So as to obtain the high rate V0 at the instant T0 of start of photography, a preliminary displacement of the grid is provided between the origin and the position X0 according to a displacement curve CB0 having a parabolic shape. In addition, after the time T1 of end of imaging, i.e., when the grid has reached the position XM, the latter returns to the zero position by a linear decline (terminal portion CB3).

The spatial derivative of the temporal variable of the curve CB illustrated in FIG. 2 is represented in FIG. 3. It is made up of two linear portions CP1 and CP2 symmetrical with respect to the axis AS passing through the midpoint (XM−X0)/2 of the area of displacement.

Such a curve profile makes it possible to reduce the visibility of the plates of the grid on the images obtained and thus to improve their quality to facilitate in particular the detection of micro-calcifications, and this regardless of the duration of exposure. In addition, the invention is free of any alternating movement, which makes it less sensitive to the mechanical parameters.

This improvement in the quality of images necessitates no modification of processing software or of image acquisition.

Additionally, displacement of the grid is generally obtained by a stepping motor which, by nature, generates mechanical oscillations during displacement. When the frequency of the oscillations corresponds to the frequency of spacing of the plates of the grid, screen peaks are obtained which are reflected in an increased visibility of the plates on the images. It was observed that the displacement profile according to an embodiment of the invention minimized this undesirable effect.

Lastly, although the invention permits distinct improvement in the quality of images with a profile of spatial derivative dx/dt made up of portions which are not necessarily linear, the visibility of the plates is reduced still further if the spatial derivative dx/dt has such linear portions.

Various modifications in structure and/or steps and/or function may be made by one skilled in the art without departing from the scope of the invention.

What is claimed is:

1. A method for improving the quality of a radiographic image of an object obtained by a radiographic X-ray unit containing an anti-diffusion grid, arranged between the object and a receiver of radiographic images, comprising the steps of displacing the grid in rectilinear translation in its plane, at the time that the image is taken, between a starting position and an ending position and according to a predetermined temporal law of displacement, wherein the law of displacement is a continuous curve exhibiting point symmetry with respect to the point whose temporal coordinate is equal to one-half of the duration of imaging, and whose spatial derivative of the temporal variable exhibits two portions symmetrical with respect to an axis of symmetry passing through the center of the area of displacement of the grid, and displacing the grid according to the law of displacement at a high rate of displacement in the vicinity of the starting position and of the ending position.

2. The method according to claim 1, wherein the high rate of displacement is between about 3 times and about 10 times the value of the ratio between the area of displacement and the duration imaging.

3. The method according to claim 1, wherein the two portions of the spatial derivative of the temporal variable are linear.

4. The method according to claim 2, wherein the two portions of the spatial derivative of the temporal variable are linear.

5. The method according to claim 1, wherein the continuous curve is formed of two portions symmetrical with respect to the point whose temporal coordinate is equal to one-half of the duration of photography, each of these portions representing a profile of evolution of the variable position, a function of the square root of the variable time.

6. The method according to claim 2, wherein the continuous curve is formed of two portions symmetrical with respect to the point whose temporal coordinate is equal to one-half of the duration of photography, each of these portions representing a profile of evolution of the variable position, a function of the square root of the variable time.

7. The method according to claim 3, wherein the continuous curve is formed of two portions symmetrical with respect to the point whose temporal coordinate is equal to one-half of the duration of photography, each of these portions representing a profile of evolution of the variable position, a function of the square root of the variable time.

8. A radiographic X-ray unit for radiographic images of an object comprising:

a source X-ray radiation to produce a beam of radiation;

a receiver of the beam of radiation;

an anti-scatter grid disposed between the source and the receiver; and means for displacing the grid in rectilinear translation in its plane, at the time the image is taken between a starting position and an ending position, according to a predetermined temporal law of displacement, the law of displacement being a continuous curve exhibiting point symmetry with respect to the point whose temporal coordinate is equal to one-half of the duration of imaging, and whose spatial derivative of the temporal variable exhibits two portions symmetrical with respect to an axis of symmetry passing through the center of the area of displacement of the grid, and the grid is displaced at a high rate of displacement in the vicinity of the starting position and of the ending position.

* * * * *